United States Patent
Ford

(10) Patent No.: US 9,572,724 B2
(45) Date of Patent: Feb. 21, 2017

(54) PRINTED WETNESS AND HEALTH INDICATORS ON ABSORBENT ARTICLES AND METHODS OF MAKING SAME

(71) Applicant: Clopay Plastic Products Company, Inc., Mason, OH (US)

(72) Inventor: Jerry Ford, Maineville, OH (US)

(73) Assignee: CLOPAY PLASTIC PRODUCTS COMPANY, INC., Mason, OH (US)

( * ) Notice: Subject to any disclaimer, the term of this patent is extended or adjusted under 35 U.S.C. 154(b) by 184 days.

(21) Appl. No.: 14/462,536

(22) Filed: Aug. 18, 2014

(65) Prior Publication Data

US 2015/0051564 A1    Feb. 19, 2015

Related U.S. Application Data

(60) Provisional application No. 61/866,678, filed on Aug. 16, 2013.

(51) Int. Cl.

| | |
|---|---|
| *A61F 13/42* | (2006.01) |
| *B41F 23/04* | (2006.01) |
| *B41F 19/00* | (2006.01) |
| *A61F 13/15* | (2006.01) |
| *B41F 5/24* | (2006.01) |

(52) U.S. Cl.
CPC ......... *A61F 13/42* (2013.01); *A61F 13/15707* (2013.01); *A61F 13/15731* (2013.01); *A61F 13/15804* (2013.01); *B41F 5/24* (2013.01); *B41F 19/008* (2013.01); *B41F 23/04* (2013.01); *A61F 2013/429* (2013.01); *Y10T 428/24273* (2015.01); *Y10T 428/249958* (2015.04); *Y10T 428/249978* (2015.04)

(58) Field of Classification Search
CPC .......................... A61F 13/42; A61F 13/15731
See application file for complete search history.

(56) References Cited

U.S. PATENT DOCUMENTS

| | | |
|---|---|---|
| 4,022,211 A | 5/1977 | Timmons et al. |
| 6,772,708 B2 | 8/2004 | Klofta et al. |
| 7,159,532 B2 | 1/2007 | Klofta et al. |
| 7,332,642 B2 | 2/2008 | Liu |
| 7,531,471 B2 | 5/2009 | Quincy, III |
| 7,687,245 B2 | 3/2010 | Lye et al. |
| 8,012,761 B2 | 9/2011 | Boga et al. |
| 8,222,476 B2 | 7/2012 | Song et al. |

(Continued)

*Primary Examiner* — Hai Vo
(74) *Attorney, Agent, or Firm* — Thompson Hine LLP

(57) ABSTRACT

A wetness indicating polymeric film and method of making the film is provided. The method includes feeding a polymer film into a flexographic printing apparatus; printing at least one wetness indicator ink onto a first side of the perforated polymer; and perforating the polymer film by forming a plurality of apertures or enlarged micropores that extend from the first side to the second side. The apertures or enlarged micropores permit a sufficient quantity of an aqueous liquid to pass from the second side through the perforated polymer film to the first side. Upon contact, the aqueous liquid reacts with the wetness indicator ink to cause a color change visible by an unaided human eye. In an absorbent article including the inventive film as a backsheet, the total amount of liquid that passes through the backsheet is negligible and the barrier properties of the backsheet as a whole are not compromised.

12 Claims, 9 Drawing Sheets

(56) References Cited

U.S. PATENT DOCUMENTS

| | | |
|---|---|---|
| 8,618,349 B2 | 12/2013 | Klofta |
| 2004/0191118 A1* | 9/2004 | Mody .................. G01N 31/222 |
| | | 422/401 |
| 2005/0234414 A1* | 10/2005 | Liu ......................... A61F 13/42 |
| | | 604/361 |
| 2008/0057534 A1 | 3/2008 | Martin et al. |
| 2008/0091156 A1 | 4/2008 | Maldonado et al. |
| 2010/0262099 A1 | 10/2010 | Klofta |
| 2010/0305529 A1 | 12/2010 | Ashton et al. |
| 2011/0015599 A1 | 1/2011 | Song et al. |
| 2011/0137274 A1 | 6/2011 | Klofta et al. |
| 2011/0144603 A1 | 6/2011 | Song |
| 2011/0152805 A1 | 6/2011 | Gil |
| 2012/0143160 A1 | 6/2012 | Song |
| 2012/0150134 A1 | 6/2012 | Wei et al. |
| 2012/0172825 A1 | 7/2012 | Ales et al. |
| 2012/0203190 A1 | 8/2012 | Song et al. |
| 2012/0308787 A1 | 12/2012 | Kozee et al. |
| 2013/0066289 A1 | 3/2013 | Song et al. |
| 2013/0158492 A1 | 6/2013 | Song et al. |
| 2013/0158493 A1 | 6/2013 | De Bruin et al. |

* cited by examiner

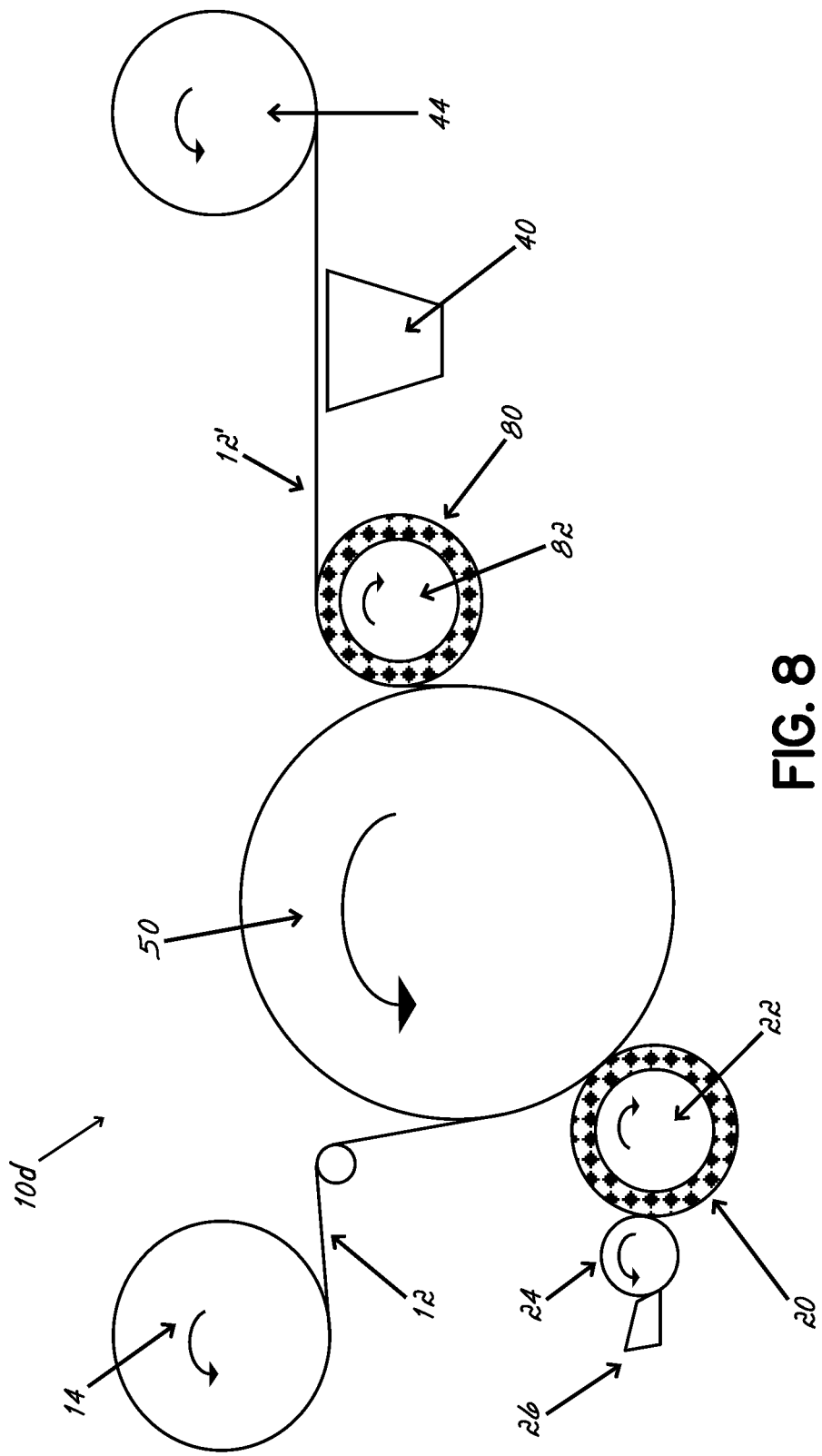

PRINTED WETNESS AND HEALTH INDICATORS ON ABSORBENT ARTICLES AND METHODS OF MAKING SAME

CROSS-REFERENCE TO RELATED APPLICATIONS

Pursuant to 37 C.F.R. §1.78(a), this application claims the benefit of and priority to prior filed, Provisional Application Ser. No. 61/866,678 filed Aug. 16, 2013, which is expressly incorporated herein by reference in its entirety.

FIELD OF THE INVENTION

The present invention is directed toward printed polymer films and methods of making these films. More particularly, the printed polymer films are printed with reactive inks that when used as a barrier layer on an absorbent article, diaper, adult incontinence pad, bandage, or similar hygiene or healthcare device, indicate wetness or other health-related information.

BACKGROUND OF THE INVENTION

In recent years, wetness indicators have come to be commonly used on absorbent articles, such as baby diapers, adult incontinence pads, and training pants, as a visual indication that the absorbent article is wet with urine. These wetness indicators generally fall into two types. One type, a dissolvable ink, is an ink which is visible while the absorbent article is dry but dissolves and becomes invisible when the absorbent article becomes wet. Another type is an ink that is either invisible or a first color when dry, but which becomes visible or changes to a second color when urine contacts the ink. Generally, these types of ink are considered non-dissolvable inks. In either case, the urine must contact the ink directly in order for the wetness indicator to perform correctly.

The purpose of a wetness indicator is to provide visual information to a caregiver that the absorbent article is wet, without the caregiver having to unfasten or remove the absorbent article. Therefore, to function correctly, the wetness indicator must be visible on the outside of the absorbent article (also called the garment side or garment-facing side). Therefore, the wetness indicator ink should be applied to the outer cover of the absorbent article, in order to be visible to a caregiver.

However, the primary function of the outer cover of an absorbent article is to act as a moisture barrier, preventing urine or other body fluids from escaping the absorbent article. Any absorbent article with an outer cover that permitted body fluids to leak out would be completely unacceptable to consumers. The outer covers of disposable absorbent articles are usually made of polymer films, which are excellent fluid barriers.

This presents the absorbent article manufacturer with a conundrum. To provide the optimal visibility, the wetness indicator ink should be on the outer cover of the absorbent article. To act as a moisture barrier, the outer cover should not allow liquids to leak out. However, to provide the caregiver with the desired visual cue, the aqueous liquid, e.g., urine, needs to directly contact the wetness indicator ink.

The previous solution to the conundrum has been to apply wetness indicator inks to the interior surface (i.e. body-facing or 'wet' side) of the polymer film that comprises an absorbent article's outer cover. This way, the urine can contact the wetness indicator ink inside the absorbent article, and the visual cue can be seen on the outside of the absorbent article without liquid leakage through the polymer film.

The polymer films used as liquid barriers in outer covers can retain more than liquid. For example, these films can also retain body heat, perspiration and moisture vapor, which can make the absorbent article hot, steamy and uncomfortable. To counter this discomfort, many absorbent article backsheets are made from microporous breathable polymer films. These films, which are well known in the art, are typically made from polymer resin that is filled with finely-divided particles of inorganic material such as calcium carbonate. A film made from this filled polymer is then stretched to cavitate the polymeric matrix around the filler particles, which creates micropores that form tortuous paths through the film. Molecules of water vapor can escape the absorbent article interior by travelling through the tortuous paths of micropores, which means that the article is more comfortable to wear.

But microporous films are also opaque or semi-opaque, because the myriad internal surfaces created within the film by the micropores reflect ambient light. Often, this opacity is a desirable property as it helps to mask the presence of urine, feces, or other body fluids within the absorbent article. However, this opacity also masks the appearance of wetness indicator inks that are printed on the interior surface of the outer cover film. Because of this masking effect, manufacturers must print wetness indicator markings that are dark or intensely colored, with heavy ink coverage, so the wetness indicator can be seen through the opaque outer cover film. In some cases, the film may be made with a lower opacity to allow the wetness indicator ink to show through, but this decrease in opacity also means the masking power of the film is reduced, potentially allowing the urine or feces to be visible through the film.

The heavy application of wetness indicator inks can lead to another problem. For example, with baby diapers, it has been found that these inks can sometimes dissolve in the baby's urine, then wick back through the absorbent core and transfer onto the baby's skin. This is both unsightly and creates an unnecessary exposure of the baby's skin to the ink components.

Finally, most disposable absorbent article outer covers are now printed with graphics that decorate and enhance its appearance. Because of the opacity problem already discussed, and to achieve the best appearance, these graphics are usually printed on the exterior (garment-facing side or 'dry' side) of the outer cover film. However, the wetness-indicator graphics have historically been printed on the interior side of the film. Therefore, the manufacturer must print graphics on both sides of the outer cover film, which can be costly. It is even more complex and costly to print the wetness indicator ink on the inside and the main diaper graphics on the outside in register with each other to achieve visually striking effects.

In view of the foregoing, a need exists for wetness-indicating polymer films having wetness-indicator (WI) inks printed on the exterior or 'dry' side of an absorbent outer cover (backsheet) film.

SUMMARY

In accordance with an embodiment, a method of making a wetness-indicating polymer film is provided. The method includes feeding a polymer film having a first side and a second side into a flexographic printing apparatus. The method further includes printing at least one wetness indicator ink onto the first side of the perforated polymer film, and perforating the polymer film by forming a plurality of apertures or enlarged micropores in the polymer film that extend from the first side to the second side. The apertures or enlarged micropores, which are in register with the printed wetness indicator ink, permit passage of a sufficient quantity of an aqueous liquid from the second side through the perforated polymer film to the first side to react with the wetness indicator ink printed onto the first side and cause the wetness indicator ink to undergo a color change visible by unaided human eye.

In accordance with another embodiment of the present invention, a method of making a wetness-indicating polymeric film is provided that includes perforating a breathable polymer film to form the plurality of apertures or enlarged micropores that extend from the first side to the second side; and printing at least one wetness indicator ink in register with the plurality of apertures or enlarged micropores onto the first side of the perforated polymer film to form a printed material. The apertures or enlarged micropores have a sufficient size to permit passage of an aqueous liquid from the second side through the perforated polymer film to the first side. The breathable polymer film may be a microporous film or a monolithic film.

Another embodiment of the present invention is a method of making a wetness-indicating polymeric film comprising forming a plurality of apertures or enlarged micropores through a polymer film using one deck of a printing press, where the plurality of apertures or enlarged micropores are selectively placed in the film to coincide with the placement of wetness indicator inks. The method further includes printing at least one wetness indicator ink in register with the plurality of apertures or enlarged micropores onto a first side of the perforated polymer film to form a printed material. The apertures or enlarged micropores permit passage of a sufficient quantity of an aqueous liquid from a wet side through the perforated polymer film to a dry side to react with the wetness indicator ink printed onto the dry side and cause the wetness indicator ink to undergo a color change visible by unaided human eye. The polymer film may be a breathable polymeric film. The breathable polymeric film may be a microporous or a monolithic film.

In accordance with another embodiment of the present invention, an absorbent article is provided that includes a top sheet; a backsheet comprising the wetness-indicating polymer film; and an absorbent layer between the top sheet and the backsheet.

BRIEF DESCRIPTION OF THE DRAWINGS

While the specification concludes with claims particularly pointing out and distinctly claiming the present invention, it is believed that the invention will be further understood from the following detailed description taken in conjunction with the accompanying drawings in which:

FIG. 8 is a schematic illustration of a flexographic printing system incorporating the perforation plate of FIG. 7, in accordance with an embodiment of the present invention.

DETAILED DESCRIPTION

Figure 1:
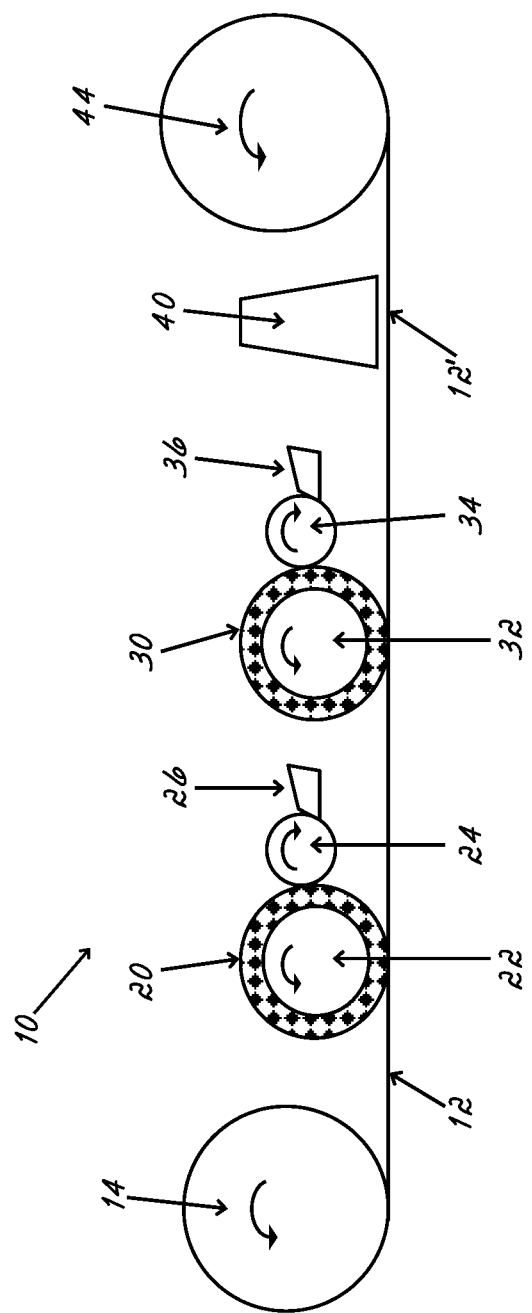
FIG. 1 is a schematic illustration of an exemplary multi-stage flexographic printing system.

The present invention is directed to barrier film materials incorporating wetness indicator inks, for use in various applications. In one embodiment, the barrier film materials are suitable for use as outer covers for absorbent articles, such as infant and toddler diapers, toddler training pants, and adult incontinent articles. However, one skilled in the art will recognize from the present description other specific applications and uses of the barrier film materials which are within the scope of the invention.

For the purpose of this disclosure, the following terms are defined:

"Film" refers to material in a sheet-like form where the dimensions of the material in the x (length) and y (width) directions are substantially larger than the dimension in the z (thickness) direction. Films typically have a z-direction thickness in the range of about 1 μm to about 30 μm. For example, the z-direction thickness may be about 1 μm, about 5 μm, about 10 μm, about 15 μm, about 20 μm, or about 25 μm, or in a range encompassed by specific combination of any two of the foregoing.

"Breathable film" refers to a polymer film, which allows the passage of water vapor from one side of the film (e.g., the 'wet' side) to the other side of the film (e.g., the 'dry' side). When used as a barrier film or outer cover on an absorbent article such a diaper, breathable films allow water vapor from urine and perspiration to escape the interior of the diaper, thereby increasing the comfort to the wearer, while also preventing or limiting the escape of body fluids from the interior of the diaper. For the present disclosure, a material is considered breathable if the material has a water vapor transmission rate (WVTR) of about 500 g/m$^2$·24 hr or more, as measured by ASTM E96A.

"Microporous film" refers to a subset of breathable polymer films, where the polymer film comprises one or more filler materials and is stretched after film formation to provide microporosity within the film. The micropores that are formed can interconnect to create tortuous paths of microscopic cavities within the film. These micropores are not readily visible to the naked eye, and typically have a maximum pore size up to about 10 microns. Typical pores sizes are about 1 μm, about 2 μm, or about 5 μm, for example. Desirably, the micropores are sufficiently small so that the microporous films prevent the passage of liquid at atmospheric pressure.

"Monolithic film," for the purpose of the present disclosure, refers to a subset of breathable polymer films where the polymer film is substantially solid and without micropores, pores, apertures, cracks, perforations, or other such openings or passages through the depth of the film, but which permit the passage of water vapor from the wet side to the dry side of the film due to the hydrophilic nature of the polymer itself. Monolithic films are typically made from polymers such as polyesters, polyamides, polyethers, etc., which have functional groups that render the polymer more hydrophilic than typical polyolefins like polyethylene and polypropylene.

"Perforated film" refers to a polymer film in which a plurality of apertures are pressed, torn, cut or punched straight through the depth of a polymer film. Apertures are not limited to any specific shape, but include openings, holes, gaps, slits, slots, cracks, or combinations thereof that extend from the first side straight through the depth of a polymer film to the second side of the film. Perforated films are contrasted with microporous films, where the micropores form tortuous paths of microscopic cavities interconnected within the film. However, for the purpose of this disclosure, a microporous film with intentionally enlarged micropores that permit the passage of small amounts of fluid at atmospheric pressure may be considered as a subset of perforated films. The apertures in the perforated films are not specifically limited to any particular size; however, for the purpose of this disclosure, perforations in these films are small in order to permit only tiny amounts of liquid to pass through the film. If the perforations in the film are too large, then significant amounts of liquid can pass through and the film becomes an ineffective wetness barrier. Typical average diameters for perforations (i.e., apertures and/or enlarged micropores) may be in a range from about 20 µm to about 300 µm. For example, average perforation size may be about 100 µm in diameter. Moreover, the desired aperture or enlarge micropore size may be dependent on the viscosity and surface tension of the ink being applied, as the desire is to have the ink fill into the aperture and traverse the film when printed over the aperture. Generally, larger perforations may be needed when the perforation is made after ink application, whereas relatively smaller perforations are preferred and can be used when made before ink application.

"Wet side" refers to the side of a barrier film on an absorbent article that faces the body of the wearer and is likely to be impinged by body fluids. For example, with a disposable diaper, the wet side of the barrier film is the side facing the body of the wearer and the absorbent core inside the diaper, where urine and feces are contained.

"Dry side" refers to the side of a barrier film on an absorbent article that is opposite the wet side. For example, with a disposable diaper, the dry side of the barrier film is the side facing away from the interior of the diaper. Instead, the dry side faces the outer garments of the wearer.

"Absorbent article" refers to a garment or other article worn by a person to absorb body fluids that are involuntarily released by the wearer, such as urine or feces. For the purpose of this disclosure, an absorbent article is specifically a disposable absorbent article, which is intended to be a single-use or limited-use article that is then discarded, as opposed to a durable article that can be cleaned and reused many times.

"Diaper," "toddler training pant," and "adult incontinence pad or undergarment" are specific types of absorbent articles.

"Backsheet" or "outer cover" are interchangeable terms referring to the barrier film used on the outside of the absorbent article. The outer cover functions to contain the other absorbent article components, contain body fluids within the absorbent article to prevent these fluids from soiling the garments, bedding or furnishings of the wearer or caretaker, and to provide a garment-like appearance to the article. For the purpose of this disclosure, "backsheet" or "outer cover" refer specifically to the barrier polymer film component, whether the film is used alone or in a multilayer composite or laminate, such as a laminate of film and a nonwoven fabric.

"Wetness indicator ink" or "WI ink" refers to any ink which, when exposed to liquids such as water, urine, blood or other bodily fluid, undergoes a color change or other visible change to indicate the presence of these liquids. Wetness indicator inks may appear to appear, disappear, or change color, but the change is readily observed by the unaided human eye. For the present invention, the term 'wetness indicator' is not limited solely to inks that indicate the presence of fluid. For the present invention, 'WI ink' also encompasses inks which undergo a color change when exposed to certain biological or chemical components in the liquid. For example, a WI ink may change color because of the presence of excessive sugar in the urine of a diabetic person.

Regarding the WI ink, there is no specific limitation with regard to any chemical species. However, as the WI ink is printed on the garment facing side of the barrier layer, it is preferred that the WI ink is not appreciably soluble in the aqueous liquid whose presence is being indicated. Non-limiting examples of WI ink, as well as matrices for non-diffusible immobilization of the ink may be found in U.S. Pat. No. 8,557,894 and U.S. Patent Application Publication No. 2013/0066289, which are incorporated herein by reference in their entirety.

It is preferred that the WI ink printing be disposed adjacent to the aperture, so that one or more edges of the WI ink printing graphic extend at least about 25% past one or more edges of the aperture. More preferably, the WI ink printed graphic extends at least about 15% and most preferably at least about 10% past one or more edges of the aperture.

In another embodiment, the WI ink may be disposed adjacent to a varnish coating. Without being limited by theory, the varnish coating serves as a sealant of sorts for the WI ink. Suitable materials for the varnish coating may be selected from the group consisting of acrylic copolymers, shellac-based acrylic resins, polyamides, and combinations thereof. These materials are intended to be exemplary but not limiting in any way. Additionally, the varnish coating may be disposed over the printed graphic formed by the WI ink, beneath the graphic, or both. Moreover, it is preferred that the varnish coating be disposed adjacent to the graphic such that one or more edges of the coating extend at least about 25% past one or more edges of the graphic. More preferably, the varnish coating extends at least about 15% and most preferably at least about 10% past one or more edges of the graphic. The varnish coating may be applied in a manner applicable to the WI ink.

The outer covers of diapers are usually made of breathable polymer films, which are excellent fluid barriers and also allow water vapor to escape to increase the diaper comfort. Either monolithic or microporous polymer films may be used to make a breathable backsheet film. Monolithic films cannot leak or allow microbes to pass through, so they provide outstanding barrier properties. But the polymers used in monolithic films are expensive when compared to the polymers typically used in microporous films. Microporous films can sometimes leak if the micropores are too large or if the body fluids on the wet side of the diaper experience a pressure surge, so they are somewhat less effective as barrier films than monolithic films. However, microporous films are typically made of relatively inexpensive polyolefin polymers and inexpensive mineral powders.

Suitable polymer compositions for use in microporous barrier films of the present invention include, but are not limited to, polyolefins such as ultra low density polyethylene (ULDPE), low density polyethylene (LDPE), linear low density polyethylene (LLDPE), medium density polyethylene (MDPE), high density polyethylene (HDPE), polypropylene homopolymers and copolymers, functionalized polyolefins, polyesters, polyamides, and the like.

Suitable fillers for use in microporous films include, but are not limited to, various organic and/or inorganic materials. In a specific embodiment, the filler may comprise one or more finely powdered inorganic materials such as metal oxides, metal hydroxides, metal carbonates and the like. Preferred fillers include, but are not limited to, calcium carbonate, barium sulfate, diatomaceous earth, talc, titanium dioxide, and mixtures thereof. The particle size of the filler may be selected in order to influence the micropore size in the microporous film and consequently the breathability of the resulting outer cover. Typically, filler having an average particle size of from about 0.5 to about 5 microns is suitable, although fillers of smaller or larger size may also be employed. For example, the average filler size may be about 1 micron to about 3, or about 1.5 micron to about 2.5 microns. The filler may optionally include a surface coating to facilitate dispersion of the filler in the polymer composition, to increase the ability of the filler to repel water, and/or to increase incompatibility of the filler with the polymer composition and the formation of micropores at the vicinity of the filler. Suitable surface coatings include but are not limited to organic acids such as stearic or behenic acid, salts of organic acids such as calcium stearate, fatty acids and salts thereof, nonionic surfactants, and similar such coatings.

The filler is included in the microporous film in an amount suitable to provide the desired breathability. Generally, the filler may be employed in an amount of from about 25 to about 75 weight percent, based on the total weight of the microporous film components.

A number of different stretching techniques known in the art may be employed to stretch the microporous film layers. For example, the film layers may be stretched by cross direction (CD) intermeshing, and/or machine direction (MD) intermeshing. Techniques to stretch films by CD or MD intermeshing are taught in U.S. Pat. No. 4,166,892. Other stretching techniques include machine direction orientation (MDO) stretching or CD tentering. In addition, CD and/or MD intermeshing may be employed with MDO and/or CD tentering, in any desired order.

For many absorbent articles, especially those used with babies and toddlers, the outer cover film is printed with decorative designs. These designs are intended to make the diaper visually appealing to the wearer and the caretaker. The printed images can also provide visual cues to the caretaker that the diaper is wet and needs to be changed. These cues come from WI inks, which appear, disappear, or change color when exposed to liquids such as urine.

As discussed previously, for a number of reasons WI inks have always been printed on the 'wet' side of the diaper backsheet. Primarily, the WI inks are printed on the wet side so they can come in direct contact with urine. However, the decorative designs on a backsheet are usually printed on the dry side, so the designs are sharp, brightly colored, and easily visible. But the use of WI inks means that the backsheet barrier film must be printed on both sides, which is a costly manufacturing method. If the manufacturer wants to apply the WI ink as part of the overall graphic design on the absorbent article, the printing on both sides must also be precisely registered. This increases the complexity and cost of printing.

The present invention allows the manufacturer to print both decorative and WI inks on the dry side of the backsheet barrier film. The present invention also allows the manufacturer to use significantly less WI ink, because the WI ink is more easily visible on the dry side than on the wet side.

For the present invention, apertures or enlarged micropores are applied to the film in precise locations to correspond to the printed areas of WI ink. By placing the apertures or enlarged micropores in these areas, it is possible to control the amount of liquid that is permitted to pass or wick through the film while maximize the contact of these liquids with the WI ink.

There are many known methods for perforating polymer films. Films of the present invention could be perforated using needles, engraved calender rolls, vacuum cylinders, lasers, or other known methods. The apertures or enlarged micropores could be located on the film to correlate with the locations of the printed WI inks. For example, an optical scanner could be used to locate the printed areas of WI ink, then the film could be laser-apertured in these locations.

One particularly suitable way to manufacture the inventive film is to perforate the film using one deck of a flexographic printing press that is used to apply the WI ink. Instead of having the traditional flexographic impression plate on this deck, the deck would have a plate specially designed to perforate the film at the same locations on the film as the WI ink is printed. The perforating plate may be temperature controlled. For example, the perforating plate may be heated above temperature of the polymer film. Aligning the perforations with the printed WI ink would be a simple registration task on a printing press.

Flexographic printing is one of the simplest methods of mechanically printing on a continuous web of material. In a flexographic printing system 10 shown in FIG. 1, the image to be printed is created on a raised impression plate 20. The impression plate is then mounted onto a roll 22. Ink is applied to the impression plate, for example with an anilox roll 24 which picks up a single color of ink from an ink containment device 26, such as a pan, and transfers the ink to the raised portions of the impression plate 20. The impression plate 20 then rotates over the material 12 to be printed (e.g., a polymer film). If a second color of ink is to be printed on the material 12, another impression plate 30 is mounted on roll 32. The second color of ink is picked up from pan 36 and applied by anilox roll 34 to the impression plate 30. Similarly, if three or more colors are desired, then additional printing decks comprising impression plates, mounting rolls, anilox rolls, etc. are used inline. Similarly, in the present invention, a WI ink can be printed onto the material 12 as described. Optionally, one or more drying units 40 may be used after each printing step or all printing steps to hasten the drying of the surface of the printed material 12'.

Figure 2:
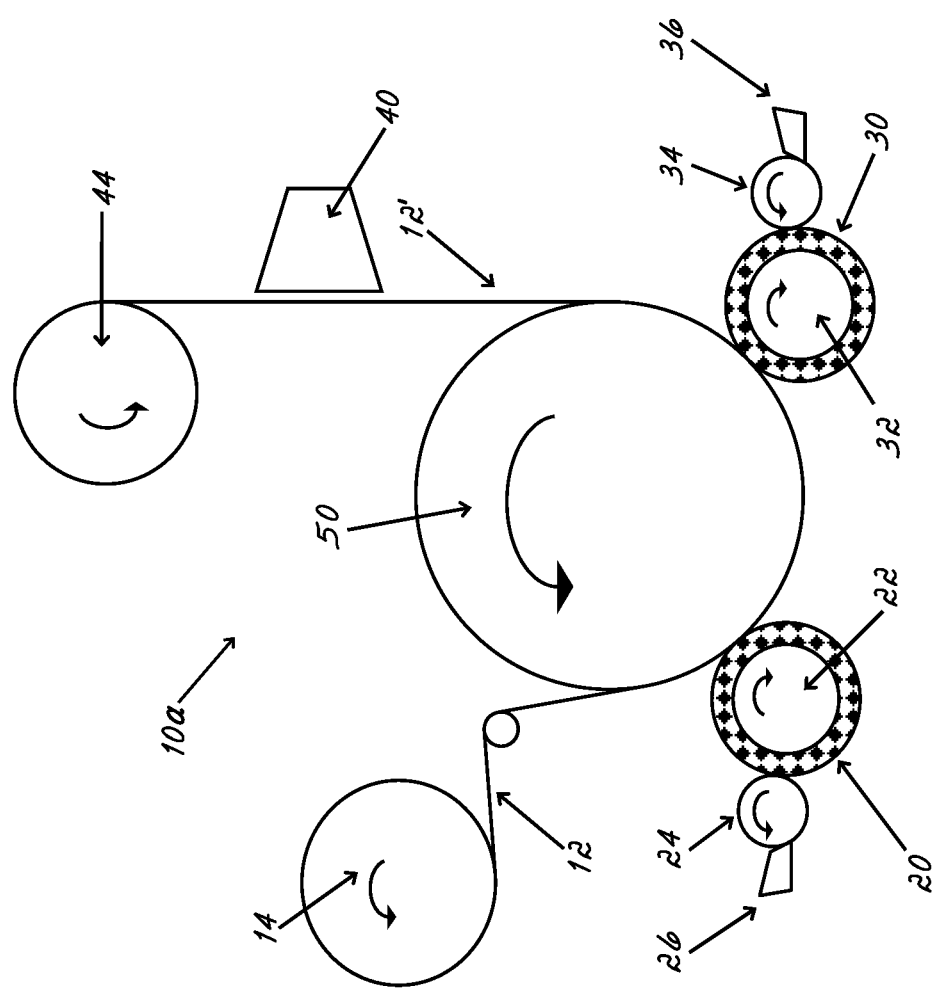
FIG. 2 is a schematic illustration of an exemplary central impression flexographic printing system.

FIG. 2 illustrates another style of flexographic printing, involving the use of a central impression (CI) drum 50. The material to be printed 12 is unwound from a roll 14 and guided by idler rolls to pass over the surface of the CI drum 50. In FIG. 2, ink from two printing decks are printed on the material 12. The ink of the first printing deck is held in pan 26, from which the ink is picked up by anilox roll 24 and transferred to the first impression plate 20 which is mounted on roll 22. The first impression plate prints the first ink pattern on the material 12. The material 12 is then carried by the CI drum 50 to the second printing deck, where the process in repeated by a second impression plate 30 on mounting roll 32 receiving ink from an ink pan 36 via an anilox roll 34. Additional printing decks can be installed around the CI drum 50, as desired. Once the printing is completed, the printed material 12' may then be treated by a drying unit 40 to hasten the drying of the printed ink, then wound into a roll 44.

For the present invention, if the film perforation step is performed on the printing press, the printing press systems illustrated in either FIG. 1 or FIG. 2 require at least two printing decks. One printing deck is used to apply the WI ink, and the other deck is used to perforate the film. Additional printing decks may be used to apply other inks, such as the colored inks used in the decorative graphics or the varnish.

The impression plates used to apply the decorative and WI inks are the plates used for standard flexographic printing and are thus well known. The impression plate used to perforate the film, though, is modified from the standard impression plate used in flexographic printing. This 'perforation plate' must be able to create apertures or enlarged micropores in the film.

The film perforation step may be performed before or after the WI ink printing step. Advantageously, if printing the WI ink is subsequent to the perforation step, the WI ink can coat and fill the apertures to control the wicking or passage of water through the film.

Figure 3:
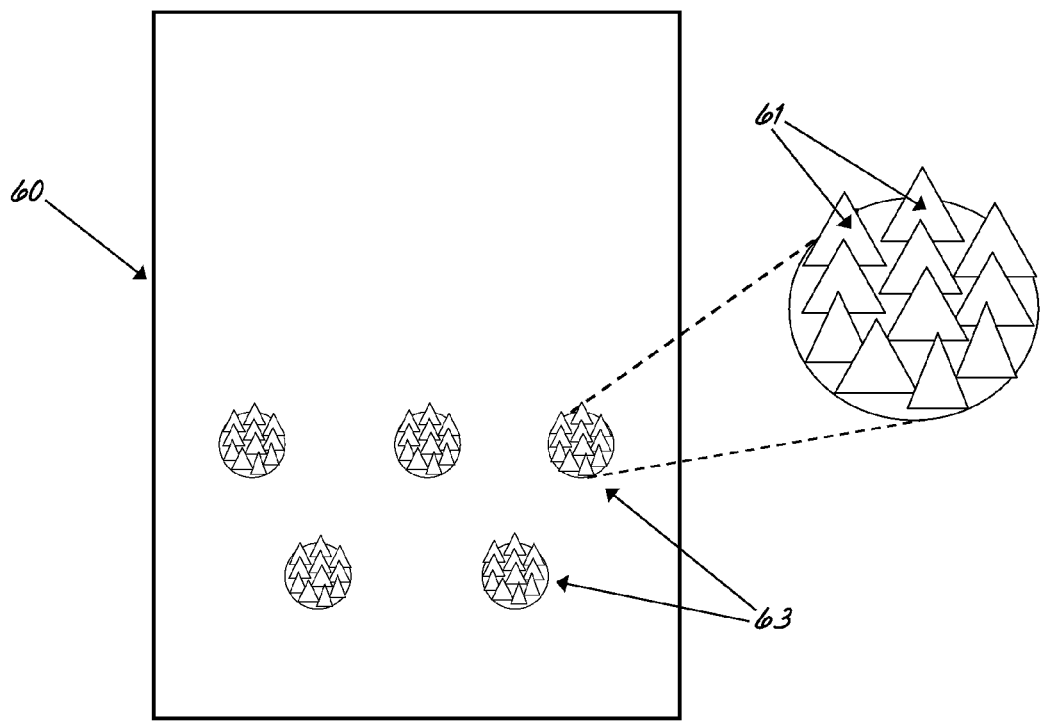
FIG. 3 is a schematic plan view of a perforation plate used in a printing deck of a flexographic printing system, in accordance with an embodiment of the present invention.
Figure 4:
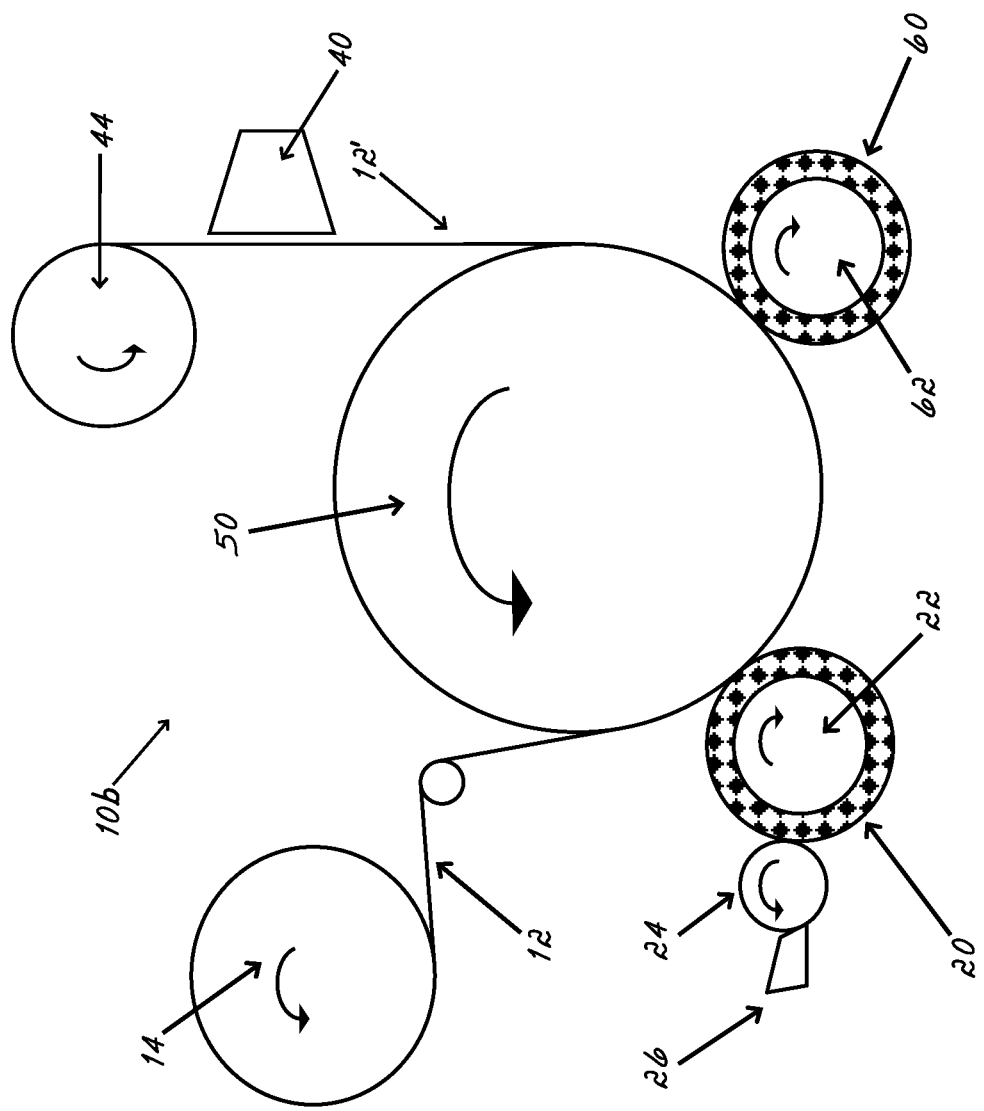
FIG. 4 is a schematic illustration of a flexographic printing system incorporating the perforation plate of FIG. 3, in accordance with an embodiment of the present invention.

FIG. 3 illustrates one embodiment of a perforation plate. The perforation plate 60 is engraved with small hard rubber points 61 that can press into the film and punch small perforations into the film. The hard rubber points 61 may be clustered into groups or zones 63 which correspond to the placement of the WI ink on the impression plate on another deck of the printing press. FIG. 4 illustrates this perforation plate in use on a printing press. The perforation plate 60 is mounted on roll 62. As the material 12 passes between the CI drum 50 and the perforation plate 60, the perforation plate 60 rotates over the material 12 and the rubber points 61 are pushed into the film, thereby creating tiny perforations in the film.

Figure 5:
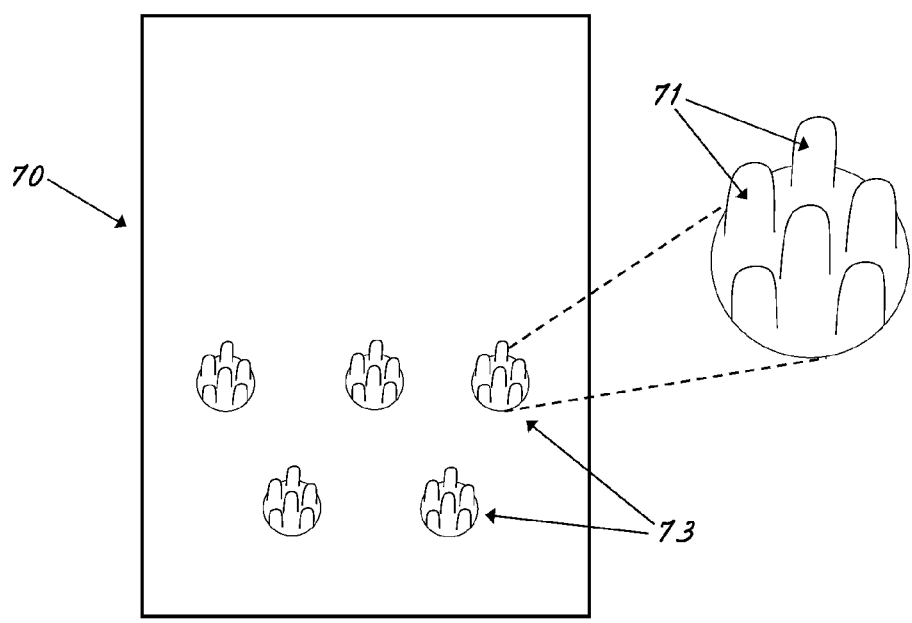
FIG. 5 is a schematic plan view of a perforation plate used in a printing deck of a flexographic printing system, in accordance with another embodiment of the present invention.

FIG. 5 illustrates another embodiment of a perforation plate. The perforation plate 70 is engraved with small rubber nubs 71 that are slightly flexible. The rubber nubs 71 may be clustered into groups or zones 73 which correspond to the placement of the WI ink on the impression plate on another deck of the printing press. When these rubber nubs encounter pressure, such as the pressure of encountering the CI drum 50, the nubs 71 will spread apart slightly. Any film pinned between the CI drum 50 and the nubs 71 will have to stretch or tear to accommodate the spreading of the nubs 71.

Figure 6:
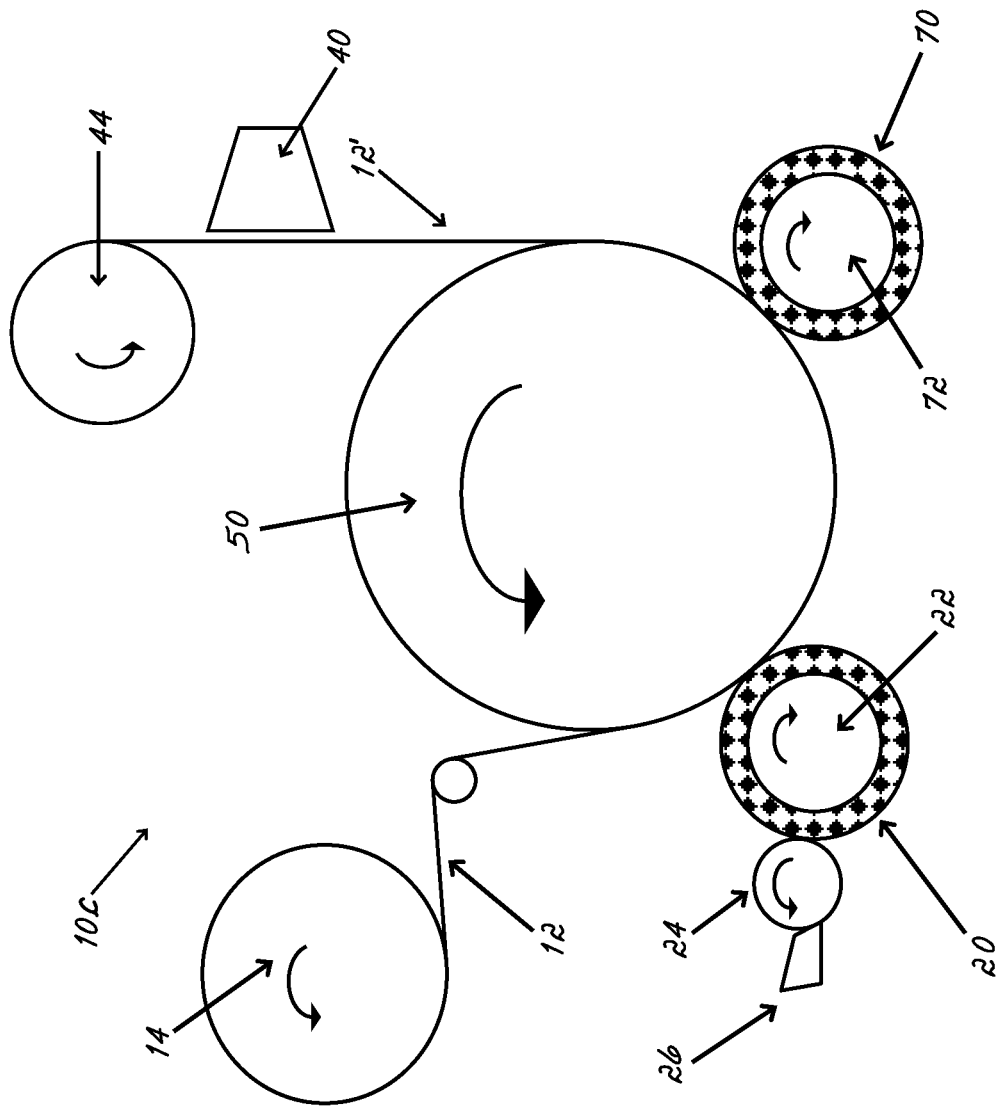
FIG. 6 is a schematic illustration of a flexographic printing system incorporating the perforation plate of FIG. 5, in accordance with an embodiment of the present invention.

FIG. 6 illustrates this perforation plate 70 in use on a printing press. The perforation plate 70 is mounted on roll 72. As the material 12 passes between the CI drum 50 and the perforation plate 70, the perforation plate 70 rotates over the material 12. As the rubber nubs 71 are pressed against the film 12 and the CI drum 50, the nubs 71 spread apart. Since the film 12 is pinned against the CI drum 50 by the nubs 71, the film 12 must stretch or tear to accommodate the spreading of the nubs 71. If the film 12 is microporous and stretches, the micropores already present in the film 12 will be enlarged. The stretching can be controlled by the flexibility of the nubs 71 to ensure that the micropores in the film 12 are enlarged sufficiently to allow the passage of small amounts of liquid in the areas stretched by the zones 73 of nubs 71. Alternatively, if the film 12 is either monolithic or microporous, and tears rather than stretches, these tears can be controlled by the flexibility of the nubs to ensure that the tears are of appropriate size to allow the passage of small amounts of liquid in the areas stretched by the zones 73 of the nubs 71.

Figure 7:
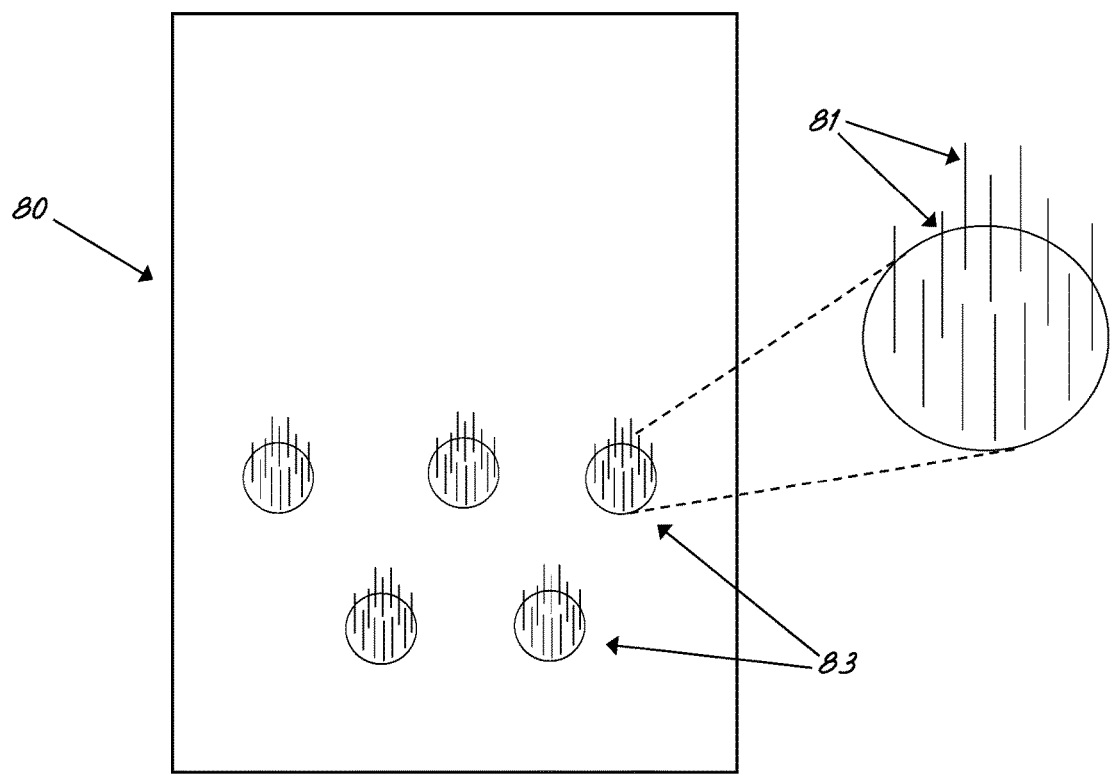
FIG. 7 is a schematic plan view of a perforation plate used in a printing deck of a flexographic printing system, in accordance with another embodiment of the present invention.

FIG. 7 illustrates another embodiment of a perforation plate. The perforation plate 80 has fine metal needles 81 that can perforate small holes in the film. The needles 81 may be clustered into groups or zones 83 which correspond to the placement of the WI ink on the impression plate on another deck of the printing press. FIG. 8 illustrates one way this perforation plate can be used on a printing press. The perforation plate 80 is mounted on roll 82. The deck containing the perforation plate 80 is positioned to replace the take-off roll where the printed film 12' exits the CI drum 50. As the material 12' passes over the perforation plate 80 under tension, the needles on the perforation plate 80 are pressed through the material 12', thereby creating tiny perforations in the film.

Figure 9A:
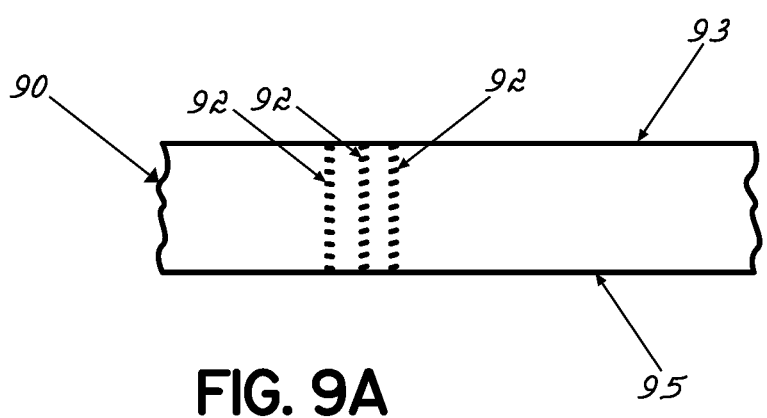
FIGS. 9A and 9B illustrate a perforated polymer film prior to and after printing with a wetness indicator (WI) ink, respectively.

In accordance with another embodiment of the present invention, the raised points, raised needles, or raise nubs may protrude from a surface of the impression plate by a distance that is equal to or greater than a thickness of the microporous polymer film, which can facilitate formation of the apertures in the polymer film. More specifically, this configuration can enable the raised protrusion (e.g., point, needle, nub, etc.) to pass completely through the thickness of the film, which facilitates formation of a perforated polymer film 90 having apertures 92 that extends completely though the film 90 from a first side 93 to a second side 95, as shown in FIG. 9A.

The film may be perforated prior to printing, thereby creating a plurality of apertures and/or expanded micropores through the film. In a second step, indicator ink may be printed on top of the perforation and some ink may be subsequently forced into the perforation. Without being bound by any particular theory, the ink within the perforation is believe to provide a conduit between the moisture inside the absorbent article and the indicator on the dry side of the absorbent article. This is believed to provide quicker migration of the moisture to the ink, thereby speeding indicator reaction.

Figure 9B:
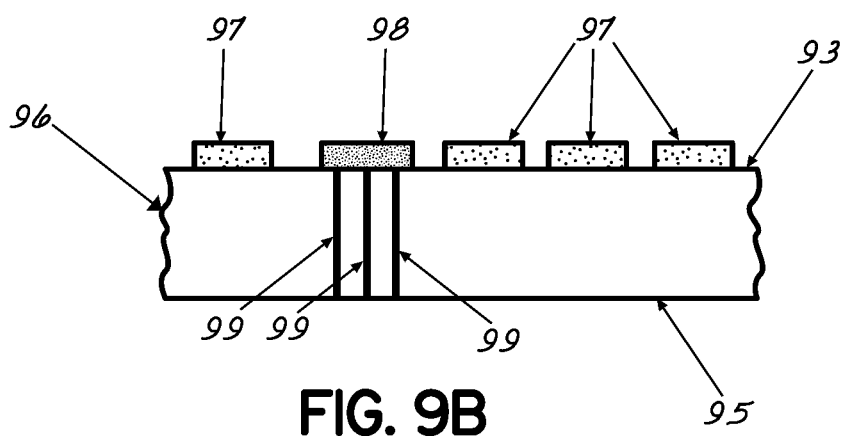
Figure 10:
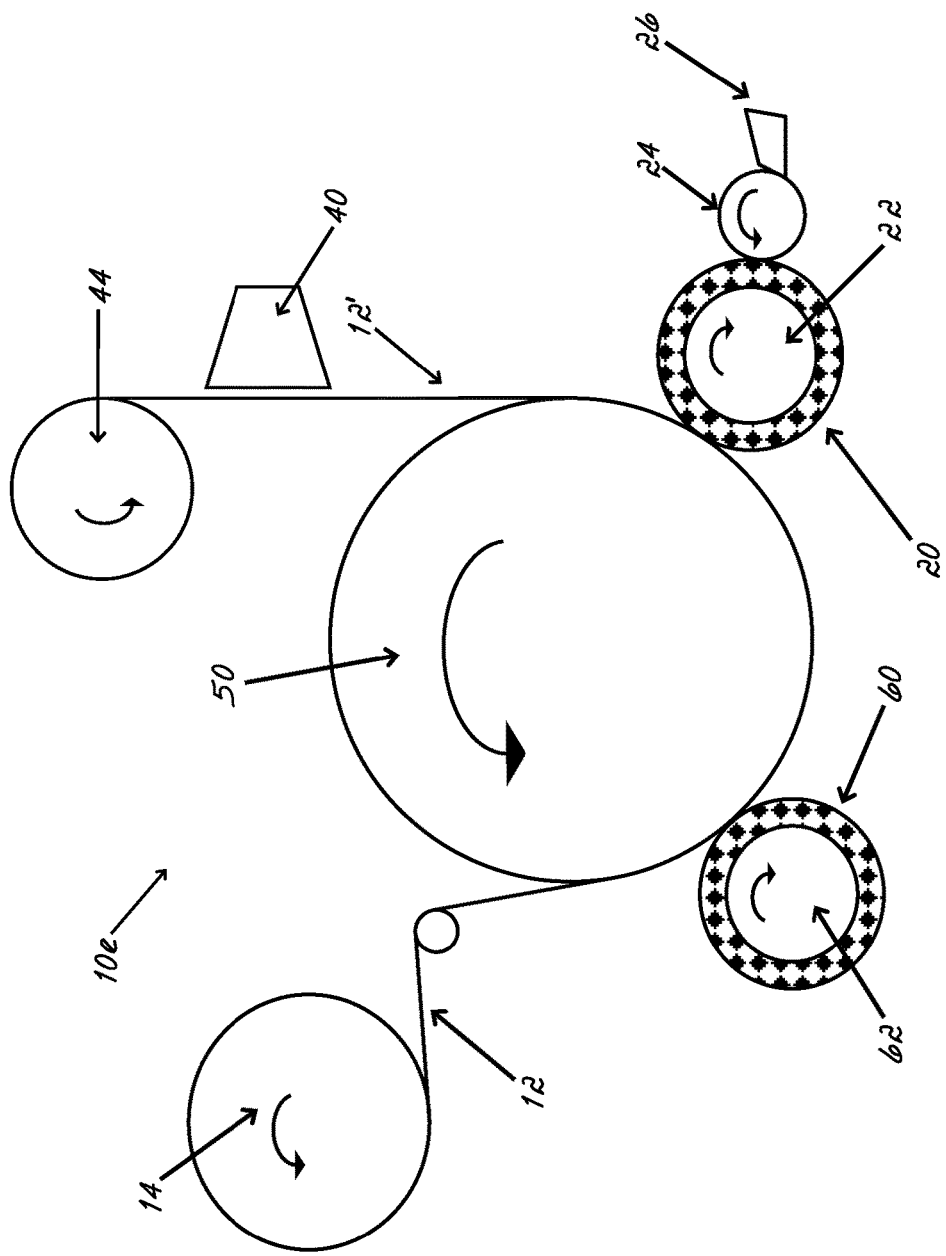
FIG. 10 is a schematic illustration of a flexographic printing system configured with a perforation deck and a printing deck in accordance with yet another embodiment of the present invention.

Accordingly, in addition to the embodiments shown in FIGS. 4, 6, and 8, the material 12 may be perforated prior to printing. For example, the directional errors of the exemplified configurations may be reversed and the heater 40 repositioned to be after printing. Alternatively, as shown in FIG. 10, perforation plate 62 and roll 60 may be repositioned relative to the printing plate array (20, 22, 24, 26) to create perforations prior to printing the WI Ink in register with the perforations. FIG. 9B depicts a wetness-indicating polymer film 96 after applying a first ink 97 and a second ink 98 to the first side 93 of the perforated polymer film 90 (from FIG. 9A). For ink applied directly to the apertures 92, ink-filled apertures 99 may be formed. Advantageously, the first and second inks 97, 98 may be WI inks, which may be adjacent to or cover the apertures.

EXAMPLE

Microporous breathable backsheet film comprising LLDPE and calcium carbonate was printed with a repeating pattern of graphics, using WI ink. The printed side of the film was designate the "dry" side, and the unprinted side of the film was designated the "wet" side. Samples of the printed backsheet film were collected and divided into two groups. For the first group, each area of the film printed with WI inks was manually perforated 10 times using a sharp, fine needle. For the second group, the films were not perforated. Drops of water were applied to the "wet" side of each film sample and allowed to sit without at ambient pressure and temperature. The WI ink on the perforated samples began to change color almost immediately, and the entire area of WI ink changed color in 15 seconds or less after the water was applied. The WI ink on the nonperforated film samples showed no color change 15 minutes after the water was applied, at which time the test was terminated.

While the present invention has been illustrated by the description of embodiments, and while the illustrative embodiments have been described in considerable detail, it is not the intention of the inventors to restrict or in any way limit the scope of the appended claims to such detail. Additional advantages and modifications readily will appear to those skilled in the art. The invention in its broader aspects is therefore not limited to the specific details, representative apparatus and methods, and illustrative examples shown and described. Accordingly, departures may be made from such details without departing from the scope of the inventors' general inventive concept.

What is claimed is:

1. A polymeric film adjacent a source of a fluid, said film having a first surface and a second surface, wherein:
    said polymeric film is a backsheet of an article;
    said first surface is a dry side, and comprises a wetness-indicating ink printed onto the first surface;
    said second surface is a wet side, and is positioned to be in contact with said fluid; and
    said polymeric film is breathable, thereby permitting water vapor to pass from the wet side to the dry side, and said polymeric film is a microporous film comprising randomly dispersed micropores with a maximum pore size of about 10 microns and comprises a plurality of perforations extending through said film from the first surface to the second surface, which have a size suitable to allow passage of an amount of liquid at atmospheric pressure, the amount being sufficient to induce a change of color in said wetness-indicating ink;
    wherein said plurality of perforations have a diameter of from about 20 microns to about 300 microns; and
    wherein said wetness-indicating ink is printed on said first surface of said polymeric film in a discontinuous pattern, and said plurality of perforations in said polymeric film are in registration with said wetness-indicating ink.

2. The polymeric film of claim 1, further comprising at least one additional ink printed onto said first surface.

3. The polymeric film of claim 2, wherein said additional ink is not a wetness-indicating ink.

4. The polymeric film of claim 1, wherein said fluid is water.

5. The polymeric film of claim 1, wherein said fluid is a bodily fluid selected from the group consisting of sweat, urine blood, feces, menses, and combinations thereof.

6. The polymeric film of claim 5, wherein said fluid comprises a substance capable of inducing a change of color in said wetness-indicating ink.

7. The polymeric film of claim 1, wherein said microporous film comprises a polyolefin selected from the group consisting of ultra low density polyethylene, low density polyethylene, linear low density polyethylene, medium density polyethylene, high density polyethylene, polypropylene copolymers and homopolymers, and combinations of any of the foregoing.

8. The polymeric film of claim 1, wherein said wetness-indicating ink is disposed adjacent to a varnish coating.

9. The polymeric film of claim 1, wherein the wetness-indicating ink is not appreciably soluble in the liquid.

10. The polymeric film of claim 1, wherein wetness-indicating ink is located in the plurality of perforations.

11. The polymeric film of claim 1, wherein the plurality of perforations are clustered into groups or zones in registration with the placement of the wetness-indicating ink.

12. The polymeric film of claim 1, wherein one or more edges of the wetness-indicating ink extend at least about 25% past one or more edges of the plurality of perforations.

* * * * *